United States Patent [19]
Prasad et al.

[11] Patent Number: 5,936,113
[45] Date of Patent: *Aug. 10, 1999

[54] PROCESS FOR MAKING O,S-DIMETHYL PHOSPHORAMIDOTHIOATE

[75] Inventors: Vidyantha A. Prasad, Leawood; Klaus Jelich, Overland Park, both of Kans.; Donald K. Smith, Liberty, Mo.

[73] Assignee: Bayer Corporation, Pittsburgh, Pa.

[*] Notice: This patent is subject to a terminal disclaimer.

[21] Appl. No.: 08/988,303

[22] Filed: Dec. 10, 1997

[51] Int. Cl.⁶ ...................................................... C07F 9/24
[52] U.S. Cl. ............................................. 558/88; 558/199
[58] Field of Search .................................................. 558/88

[56] References Cited

U.S. PATENT DOCUMENTS

| | | | |
|---|---|---|---|
| 3,309,266 | 3/1967 | Magee | 558/199 X |
| 3,639,547 | 2/1972 | Magee | 558/88 |
| 3,649,723 | 3/1972 | Magee | 558/201 |

*Primary Examiner*—Michael G. Ambrose
*Attorney, Agent, or Firm*—Joseph C. Gil; Carol Marmo

[57] ABSTRACT

The present invention provides a method for making O,S-dimethyl phosphoramidothioate. In accordance with that process, a mixture containing O,S-dimethyl phosphoramidothioate is lagered at a temperature of from 35° C. to about 45° C. for from about 3 to about 6 hours.

7 Claims, No Drawings

PROCESS FOR MAKING O,S-DIMETHYL PHOSPHORAMIDOTHIOATE

TECHNICAL FIELD OF THE INVENTION

The field of this invention is phosphoramidothioate insecticides. More particularly, the present invention pertains to a process for making O,S-dimethyl phosphoramidothioate.

BACKGROUND OF THE INVENTION

O,S-dialkyl phosphoramidothioates are effective insecticides. One particularly effective insecticide is O,S-dimethyl phosphoramidothioate (See, e.g., U.S. Pat. Nos. 3,309,266, 3,639,547 and 3,649,723, the disclosures of which are incorporated herein by reference). U.S. Pat. No. 3,309,266 discloses that O,S-dimethyl phosphoramidothioate can be made by reacting O,O-dimethyl chlorophosphorothioate with ammonia or a primary alkylamine and then heating the product of that reaction in the presence of an alkylating reagent such as an alkyl halide.

U.S. Pat. No. 3,639,547 discloses that O,S-dimethyl phosphoramidothioate can be made by reacting O,O-dimethyl phosphoramidothioate with the dimethyl ester of sulfuric acid or with a methyl ester of organic sulfonic acids. The reaction occurs at a temperature of from about 20° C. to about 100° C. In a manner similar to the method disclosed in U.S. Pat. No. 3,309,266, the O,O-dimethyl phosphoramidothioate can be made via ammoniation of a O,O-dimethyl halophosphorothioate.

With either of the above methods, the yield and purity of the formed O,S-dimethyl phosphoramidothioate are low, ranging from about 30 to 75 percent. There continues to be a need in the art, therefore for an efficient method for making O,S-dimethyl phosphoramidothioate.

BRIEF SUMMARY OF THE INVENTION

The present invention provides a method for increasing the yield and purity of O,S-dimethyl phosphoramidothioate. In accordance with the present process, a mixture containing O,S-dimethyl phosphoramidothioate is lagered at a temperature of from about 35 to about 45° C. (and preferably about 40° C.) for about 3 to 6 hours. The use of such the lagering step results in at least a 2 percent increase in yield as well as purity when compared to conventional processes.

The mixture containing O,S-dimethyl phosphoramidothioate is prepared by reacting O,O-dimethyl phosphoramidothioate in an isomerizer with a catalyst at a temperature of from about 20° C. to about 100° C. The time needed for this isomerization reaction depends on the reaction temperature and can vary from 1–2 days (at 20° C.) to a few minutes (at 100° C.). A preferred catalyst for the isomerization reaction is dimethyl sulfate (dimethyl sulfate is a derivative of sulfuric acid).

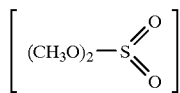

DETAILED DESCRIPTION OF THE INVENTION

In accordance with the present process, a mixture containing O,S-dimethyl phosphoramidothioate is lagered at a temperature of from about 35 to about 45° C. (and preferably about 40° C.) for about 3 to about 6 hours. The use of such a lagering step results in at least a 2 percent increase in yield over conventional processes which do not use such a step. As is well known in the art, the term "lagering" or its grammatical equivalent, means heating with agitation. In the most preferred embodiment, the agitation is provided using a suitable stirring device such as an axial flow impeller, a radial-flow impeller or an axial flow impeller/baffled tank combination, operating at a speed of from 200 to 400 revolutions per minute. Thus, the present process provides for heating a mixture containing O,S-dimethyl phosphoramidothioate at a temperature of from about 35 to about 45° C. (and preferably about 40° C.), with agitation for from about 3 to about 6 hours, and preferably for about 4 hours.

The mixture containing O,S-dimethyl phosphoramidothioate can be obtained by any means well known in the art. Typically, that mixture is prepared by reacting O,O-dimethyl phosphoramidothioate in an isomerizer with a catalyst at a temperature of from about 20° C. to about 100° C. The time needed for this isomerization reaction depends on the reaction temperature and can vary from 1–2 days (at 20° C.) to a few minutes (at 100° C.).

Suitable catalysts are the dimethyl ester of sulfuric acid or a methyl ester of an organic sulfonic acid. Exemplary such catalysts are dimethyl sulfoxide (DMSO), methyl methanealkanesulfonates such as methyl methanesulfonate, methyl ethanesulfonate, methyl propane-sulfonate, methyl hexanesulfonate, methyl benzenesulfonate, methyl toluenesulfonate, methyl xylenesulfonate, methyl napthylsulfonate, methyl p-chlorophenylsulfonate, methyl o-chlorophenylsulfonate, methyl m-bromophenylsulfonate, methyl p-bromophenylsulfonate and methyl chloronapthylsulfonate. Dimethyl sulfate is most preferred.

O,O-Dimethyl phosphoramidothioate is used to make O,S-dimethyl phosphoramidothioate and can be prepared using any process well known in the art. In one embodiment, O,O-dimethyl phosphoramidothioate is made via ammoniation of a O,O-dimethylhalophosphorothioate such as O,O-dimethylchlorophosphorothioate (DMPCT). Typically, the DMPCT in an aromatic solvent such as toluene, benzene or xylene is reacted with ammonia. The solvent is removed prior to the methylationisomerization step set forth above.

The Example that follows illustrates a preferred embodiment of the present invention and is not limiting of the specification and claims in any way.

EXAMPLES

Example 1
Preparation of O,S-Dimethyl Phosphoramidothioate

O,O-Dimethyl phosphoramidothioate was placed in an isomerizer together with Dimethyl Sulfate. The reaction was heated to a temperature of about 70° C. and maintained at that temperature for 1 to 2 hours. After 2 hours, the reaction product was split into two equal parts. One part was cooled to room temperature and maintained, with agitation, at that temperature for 12 to 18 hours (overnight). The second part of the reaction mixture was cooled to a temperature of 40° C. and maintained at that temperature, with agitation, for about 4 hours. The content of O,S-dimethyl phosphoramidothioate was determined in each part.

With overnight lagering at room temperature, the net yield of O,S-dimethyl phosphoramidothioate produced was about 78%. In contrast, with lagering at 40° C. for 4 hours, the net yield of O,S-dimethyl phosphoramidothioate was substantially greater, averaging about 82%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for making O,S-dimethyl phosphoramidothioate comprising lagering a mixture containing O,S-dimethyl phosphoramidothioate at a temperature of from about 35 to about 45° C. for from about 3 to about 6 hours, wherein agitation of said lagering step is provided by a stirring device operating at a speed of from 200 to about 400 revolutions per minute.

2. The process of claim 1, wherein said temperature is about 40° C.

3. The process of claim 1 wherein the mixture containing O,S-dimethyl phosphoramidothioate is obtained by reacting O,O-dimethyl phosphoramidothioate in an isomerizer with a catalyst at a temperature of from about 20° C. to about 100° C.

4. The process of claim 3 wherein the catalyst is dimethyl sulfate.

5. The process of claim 3 wherein the O,O-dimethyl phosphoramidothioate is made by ammoniating O,O-dimethylchlorophosphorothioate.

6. A process of making O,S-dimethyl phosphoramidothioate comprising the steps of:

a) ammoniating O,O-dimethylchlorophosphorothioate to form O,O-dimethyl phosphoramidothioate;

b) isomerizing the O,O-dimethyl phosphoramidothioate in the presence of dimethyl sulfate to form a mixture containing O,S-dimethyl phosphoramidothioate; and c) lagering the isomeric mixture of O,S-dimethyl phosphoramidothioate at a temperature of from about 35 to about 45° C. for from about 3 to about 6 hours wherein agitation of said lagering step is provided by a stirring device operating at a speed of from 200 to about 400 revolutions per minute.

7. The process of claim 6 wherein the temperature of step c) is about 40° C.

* * * * *